United States Patent [19]
Edwards et al.

[11] Patent Number: 5,514,131
[45] Date of Patent: May 7, 1996

[54] METHOD FOR THE ABLATION TREATMENT OF THE UVULA

[75] Inventors: Stuart D. Edwards, 1681 Austin Ave., Los Altos, Calif. 94024; David L. Douglass, 545 Albion Ave., Woodside, Calif. 94062

[73] Assignees: Stuart D. Edwards, Los Altos; David L. Douglass, Woodside, Calif.

[21] Appl. No.: 311,097

[22] Filed: Sep. 23, 1994

Related U.S. Application Data

[63] Continuation-in-part of Ser. No. 929,638, Aug. 12, 1992, abandoned, Ser. No. 12,370, Feb. 2, 1993, Pat. No. 5,370,675, Ser. No. 62,364, May 13, 1993, Pat. No. 5,435,805, Ser. No. 61,647, May 13, 1993, Pat. No. 5,421,819, Ser. No. 61,072, May 14, 1993, Pat. No. 5,385,544, and Ser. No. 239,658, May 9, 1994, Pat. No. 5,456,662.

[51] Int. Cl.⁶ .................................................. A61B 17/39
[52] U.S. Cl. ............................ 606/45; 606/41; 607/101; 607/134; 128/898
[58] Field of Search ............................ 606/27–34, 37–42, 606/45–52, 110, 111; 604/21, 22; 607/96–102, 134, 135, 154, 156

[56] References Cited

U.S. PATENT DOCUMENTS

| | | |
|---|---|---|
| 32,066 | 1/1986 | Leveen . |
| 1,562,460 | 11/1925 | McFee ........................................ 606/49 |
| 1,741,461 | 12/1989 | Herman ...................................... 606/49 |
| 1,879,249 | 9/1932 | Hansaker . |
| 1,919,543 | 7/1993 | Doane ........................................ 606/49 |
| 1,943,543 | 1/1934 | McFadden .................................. 606/49 |
| 1,950,788 | 3/1934 | Ewerhardt et al. . |
| 1,968,997 | 8/1934 | Drucker . |
| 2,008,526 | 7/1935 | Wappler et al. . |
| 2,022,065 | 11/1935 | Wappler . |

(List continued on next page.)

FOREIGN PATENT DOCUMENTS

| | | |
|---|---|---|
| 0370890 | 5/1990 | European Pat. Off. . |
| 0453071 | 10/1991 | European Pat. Off. . |

(List continued on next page.)

OTHER PUBLICATIONS

Standard Urology Product Catalog, CIRCON ACMI: Stanford (1992).
Chang, Raymond J. et al, American Heart Journal, 125: 1276–1283 (May, 1993).
Cosman, Eric R. et al., Sterostatic and Functional Neurosurgery, pp. 2490–2499 (Date Unknown).
Diasonics, Brochure DIA 2000 171 CRF May 1988.
Perinchery Narayan, "Neoplasms of the Prostate Gland," pp. 378–409. (Date Unklnown).
Urology 5th ed., Storz, Jan. 1992.
Transuretheral wave Thermotherapy for Prostatism: Early Mayo Foundation Experience: Blute, May Clinic Proceedings: vol. 67 May 1992, pp. 417–421.
New Therapies for Benign Prostatic Hyperplasia, Editorial Bruskewitz, May Clinic Proceedings vol. 67 May 92, pp. 493–495.
Industry Strategies, Urology: "A Multi Billion Dollar Market . . ." Stephen Scala Nov. 19, 1991 pp. 1–32.
U. I. Dept. of Health and Human Services, MMWR 41: 401–404 vol. 41, No. 23, (Jun. 12, 1992).

*Primary Examiner*—Stephen C. Pellegrino
*Assistant Examiner*—Michael Peffley
*Attorney, Agent, or Firm*—Haynes & Davis

[57] ABSTRACT

A method of medical ablation of tissue accessible thorough the mouth or nose is disclosed having the steps of: a) inserting a probe through the mouth into the oral cavity, wherein said probe has a disposable electrode enclosed within an insulating sleeve bendable therewith; b) steering said probe through the oral cavity into close proximity to the tissue; c) extending the disposable electrode and the insulating sleeve out of the probe and penetrating the tissue; and d) applying RF energy to the tissue surrounding the electrode to effect ablation of said tissue.

16 Claims, 12 Drawing Sheets

U.S. PATENT DOCUMENTS

| | | |
|---|---|---|
| 2,047,535 | 7/1936 | Wappler . |
| 2,118,631 | 5/1938 | Wappler . |
| 2,710,000 | 6/1955 | Cromer et al. . |
| 3,230,957 | 1/1966 | Seifert . |
| 3,339,542 | 9/1967 | Howell . |
| 3,556,079 | 1/1971 | Omizo et al. . |
| 3,595,239 | 7/1971 | Petersen . |
| 3,598,108 | 8/1971 | Jamshidi . |
| 3,682,162 | 8/1972 | Colyer . |
| 3,828,780 | 8/1974 | Morrison, Jr. . |
| 3,835,842 | 9/1974 | Iglesias . |
| 3,840,016 | 10/1974 | Lindemann . |
| 3,850,175 | 11/1974 | Iglesias . |
| 3,858,577 | 1/1975 | Bass et al. . |
| 3,884,237 | 5/1975 | O'Malley et al. . |
| 3,924,628 | 12/1975 | Droegemueller et al. . |
| 3,939,840 | 2/1976 | Storz . |
| 3,941,121 | 3/1976 | Olinger et al. . |
| 3,942,530 | 3/1976 | Northeved . |
| 3,948,270 | 4/1976 | Hasson . |
| 3,991,770 | 11/1976 | Leveen . |
| 4,011,872 | 3/1977 | Komiya . |
| 4,119,102 | 10/1978 | Leveen . |
| 4,121,592 | 10/1978 | Whalley . |
| 4,136,566 | 1/1979 | Christensen . |
| 4,137,920 | 2/1979 | Bonnet . |
| 4,154,246 | 5/1979 | Leveen . |
| 4,204,549 | 5/1980 | Paglione . |
| 4,224,929 | 9/1980 | Furihata . |
| 4,228,809 | 10/1980 | Paglione . |
| 4,237,898 | 12/1980 | Whalley . |
| 4,267,828 | 5/1981 | Matsuo . |
| 4,295,467 | 10/1981 | Mann et al. . |
| 4,307,720 | 12/1981 | Weber, Jr. . |
| 4,311,145 | 1/1982 | Esty et al. . |
| 4,311,154 | 1/1982 | Sterzer et al. . |
| 4,312,364 | 1/1982 | Convert et al. . |
| 4,336,809 | 6/1982 | Clark . |
| 4,375,220 | 3/1983 | Matvias . |
| 4,397,314 | 8/1983 | Vaguine . |
| 4,402,311 | 9/1983 | Hattori . |
| 4,405,314 | 9/1983 | Cope . |
| 4,411,266 | 10/1988 | Cosman . |
| 4,448,198 | 5/1984 | Turner . |
| 4,452,236 | 6/1984 | Utsugi . |
| 4,470,407 | 9/1984 | Hussein . |
| 4,494,539 | 1/1985 | Zenitani et al. . |
| 4,552,554 | 11/1985 | Could et al. . |
| 4,562,838 | 1/1986 | Walker . |
| 4,565,200 | 1/1986 | Cosman . |
| 4,568,329 | 2/1986 | Mahurkar . |
| 4,580,551 | 4/1986 | Siegmund et al. . |
| 4,594,074 | 6/1986 | Anderson et al. . |
| 4,601,296 | 7/1986 | Yerushalmi . |
| 4,612,940 | 9/1986 | Kasevich et al. . |
| 4,658,836 | 4/1987 | Turner . |
| 4,660,560 | 4/1987 | Klein . |
| 4,669,475 | 6/1987 | Turner . |
| 4,672,962 | 6/1987 | Hershenson . |
| 4,676,258 | 6/1987 | Inokuchi et al. . |
| 4,681,122 | 7/1987 | Winters et al. . |
| 4,682,596 | 7/1987 | Bales et al. . |
| 4,697,595 | 10/1987 | Breyer et al. . |
| 4,700,716 | 10/1987 | Kasevich et al. . |
| 4,706,681 | 11/1987 | Breyer et al. . |
| 4,709,698 | 12/1987 | Johnston et al. . |
| 4,719,914 | 1/1988 | Johnson . |
| 4,753,223 | 6/1988 | Bremer . |
| 4,765,331 | 8/1988 | Petruzzi et al. . |
| 4,769,005 | 9/1988 | Ginsburg et al. . |
| 4,774,949 | 10/1988 | Fogarty . |
| 4,776,086 | 10/1988 | Kasevich et al. . |
| 4,781,186 | 11/1988 | Simpson et al. . |
| 4,784,638 | 11/1988 | Ghajar et al. . |
| 4,785,829 | 11/1988 | Convert et al. . |
| 4,798,215 | 1/1989 | Turner . |
| 4,800,899 | 1/1989 | Elliott . |
| 4,805,616 | 2/1989 | Pao . |
| 4,813,429 | 3/1989 | Eshel et al. . |
| 4,817,601 | 4/1989 | Roth et al. . |
| 4,818,954 | 4/1989 | Flachenecker et al. . |
| 4,822,333 | 4/1989 | Lavarenne . |
| 4,823,791 | 4/1989 | D'Amelio et al. . |
| 4,823,812 | 4/1989 | Eshel et al. . |
| 4,860,744 | 8/1989 | Johnson et al. . |
| 4,865,047 | 9/1989 | Chou et al. . |
| 4,872,458 | 10/1989 | Kanehira et al. . |
| 4,887,615 | 12/1989 | Taylor . |
| 4,893,623 | 1/1990 | Rosenbluth . |
| 4,896,671 | 1/1990 | Cunningham et al. . |
| 4,898,577 | 2/1990 | Badger . |
| 4,905,667 | 3/1990 | Foerster et al. . |
| 4,906,230 | 3/1990 | Maloney et al. . |
| 4,907,759 | 3/1990 | Cosman . |
| 4,911,148 | 5/1990 | Sosnowski et al. . |
| 4,911,173 | 3/1990 | Terwilliger . |
| 4,919,129 | 4/1990 | Weber, Jr. et al. . |
| 4,920,978 | 5/1990 | Colvin ................................ 607/154 |
| 4,932,958 | 6/1990 | Reddy et al. . |
| 4,936,281 | 6/1990 | Stasz . |
| 4,940,064 | 7/1990 | Desai . |
| 4,943,290 | 7/1990 | Rexroth . |
| 4,946,449 | 8/1990 | Davis Jr. . |
| 4,949,706 | 8/1990 | Thon . |
| 4,950,267 | 8/1990 | Ishihara et al. . |
| 4,955,377 | 9/1990 | Lennox et al. . |
| 4,961,435 | 10/1990 | Kitagawa et al. . |
| 4,966,597 | 10/1990 | Cosman . |
| 4,967,765 | 11/1990 | Turner et al. . |
| 4,982,724 | 1/1991 | Saito et al. . |
| 4,994,062 | 2/1991 | Nishigaki et al. . |
| 4,998,932 | 3/1991 | Rosen et al. . |
| 4,998,933 | 3/1991 | Eggers et al. ........................ 606/41 |
| 5,002,558 | 3/1991 | Klein et al. . |
| 5,003,991 | 4/1991 | Takayama et al. . |
| 5,007,437 | 4/1991 | Sterzer . |
| 5,007,908 | 4/1991 | Rydell . |
| 5,010,886 | 4/1991 | Passafaro et al. . |
| 5,026,959 | 6/1991 | Ito et al. . |
| 5,029,588 | 7/1991 | Yock et al. . |
| 5,030,227 | 7/1991 | Rosenbluth et al. . |
| 5,035,695 | 7/1991 | Weber, Jr. et al. . |
| 5,035,696 | 7/1991 | Rydell . |
| 5,045,056 | 9/1991 | Behl . |
| 5,045,072 | 9/1991 | Castillo . |
| 5,055,109 | 10/1991 | Gould et al. . |
| 5,057,105 | 10/1991 | Malone et al. . |
| 5,057,106 | 10/1991 | Kasevich et al. . |
| 5,057,107 | 10/1991 | Parins . |
| 5,059,851 | 10/1991 | Corl et al. . |
| 5,060,660 | 10/1991 | Gambale et al. . |
| 5,071,418 | 12/1991 | Rosenbaum . |
| 5,080,660 | 1/1992 | Buelna . |
| 5,083,565 | 1/1992 | Parins . |
| 5,084,044 | 1/1992 | Quint . |
| 5,100,423 | 3/1992 | Fearnot . |
| 5,108,415 | 4/1992 | Pinchuk et al. . |
| 5,109,859 | 5/1992 | Jenkins . |
| 5,116,615 | 5/1992 | Gokcen et al. . |
| 5,120,316 | 6/1992 | Morales et al. . |
| 5,122,137 | 6/1992 | Lennox . |
| 5,135,525 | 8/1992 | Biscoping et al. . |

| | | |
|---|---|---|
| 5,150,717 | 9/1992 | Rosen et al. . |
| 5,170,787 | 12/1992 | Lindegren . |
| 5,178,620 | 1/1993 | Eggers et al. . |
| 5,179,962 | 1/1993 | Dutcher et al. . |
| 5,190,539 | 3/1993 | Fletcher et al. . |
| 5,195,965 | 3/1993 | Shantha . |
| 5,195,968 | 3/1993 | Lundquist et al. . |
| 5,197,963 | 3/1993 | Parins . |
| 5,201,732 | 4/1993 | Parins et al. . |
| 5,207,672 | 5/1993 | Roth . |
| 5,220,927 | 6/1993 | Astrahan et al. . |
| 5,222,953 | 6/1993 | Dowlatshahi . |
| 5,228,441 | 7/1993 | Lundquist . |
| 5,234,004 | 8/1993 | Hascoet et al. . |
| 5,235,964 | 8/1993 | Abenaim . |
| 5,249,585 | 10/1993 | Turner et al. . |
| 5,254,088 | 10/1993 | Lundquist et al. . |
| 5,257,451 | 11/1993 | Edwards et al. . |
| 5,273,524 | 12/1993 | Fox et al. . |
| 5,273,535 | 12/1993 | Edwards et al. . |
| 5,275,162 | 1/1994 | Edwards et al. . |
| 5,281,213 | 1/1994 | Milder et al. . |
| 5,281,217 | 1/1994 | Edwards et al. . |
| 5,281,218 | 1/1994 | Imran . |
| 5,287,845 | 2/1994 | Faul et al. . |
| 5,290,286 | 3/1994 | Parins . |
| 5,293,868 | 3/1994 | Nardella . |
| 5,293,869 | 3/1994 | Edwards et al. . |
| 5,299,559 | 4/1994 | Bruce et al. . |
| 5,300,068 | 4/1994 | Rosar et al. . |
| 5,300,069 | 4/1994 | Hunsberger et al. . |
| 5,300,070 | 4/1994 | Gentelia et al. . |
| 5,300,099 | 4/1994 | Rudie . |
| 5,301,687 | 4/1994 | Wong et al. . |
| 5,304,134 | 4/1994 | Kraus et al. . |
| 5,304,214 | 4/1994 | Deford . |
| 5,309,910 | 5/1994 | Edwards et al. . |
| 5,312,392 | 5/1994 | Hofstetter et al. . |
| 5,313,943 | 5/1994 | Houser et al. . |
| 5,403,311 | 4/1995 | Abele et al. ............................... 606/45 |
| 5,423,812 | 6/1995 | Ellman ...................................... 606/45 |

FOREIGN PATENT DOCUMENTS

| | | |
|---|---|---|
| 0495443 | 7/1992 | European Pat. Off. . |
| 521264A2 | 1/1993 | European Pat. Off. . |
| 2848484 | 5/1979 | Germany . |
| 3218314 | 6/1983 | Germany . |
| 3844131 | 12/1988 | Germany . |
| 3838840 | 5/1990 | Germany . |
| 9007303 | 7/1990 | WIPO . |
| 9116859 | 11/1991 | WIPO . |
| 9207622 | 5/1992 | WIPO . |
| 9221285 | 12/1992 | WIPO . |
| 9921278 | 12/1992 | WIPO . |
| 9304727 | 4/1993 | WIPO . |
| 9308755 | 5/1993 | WIPO . |
| 9308756 | 10/1993 | WIPO . |
| 9308757 | 10/1993 | WIPO . |
| 9320767 | 10/1993 | WIPO . |
| 9320768 | 10/1993 | WIPO . |
| 9320886 | 10/1993 | WIPO . |
| 9320893 | 10/1993 | WIPO . |
| 9403759 | 2/1994 | WIPO . |
| 9404222 | 3/1994 | WIPO . |
| 9405226 | 3/1994 | WIPO . |
| 9406377 | 3/1994 | WIPO . |
| 9407410 | 4/1994 | WIPO . |
| 9407411 | 4/1994 | WIPO . |
| 9407412 | 4/1994 | WIPO . |
| 9407413 | 4/1994 | WIPO . |
| 9407441 | 4/1994 | WIPO . |
| 9407446 | 4/1994 | WIPO . |
| 9407549 | 4/1994 | WIPO . |

METHOD FOR THE ABLATION TREATMENT OF THE UVULA

RELATIONSHIP TO APPLICATIONS

This application is a continuation-in-part of application Ser. No. 07/929,638 filed Aug. 12, 1992, abandoned, Ser. No. 08/012,370 filed Feb. 2, 1993, now U.S. Pat. No. 5,370,675, Ser. No. 08/062,364 filed May 13, 1993, now U.S. Pat. No. 5,435,805, Ser. No. 08/061,647 filed May 13, 1993, now U.S. Pat. No. 5,421,819, Ser. No. 08/061,072 filed May 14, 1993, now U.S. Pat. No. 5,385,544, and Ser. No. 08/239,658 filed May 9, 1994, now U.S. Pat. No. 5,456,662. The entire contents of each of the above applications being hereby incorporated by reference.

FIELD OF THE INVENTION

This invention relates generally to a method and device for the treatment of the uvula, tonsils, adenoids and sinus tissue. In particular, the invention relates to an RF ablative device and method for treatment of the uvula, tonsils, adenoids, or sinus tissue.

BACKGROUND OF THE INVENTION

Treatment of cellular tissues usually requires direct contact of target tissue with a medical instrument, usually by surgical procedures exposing both the target and intervening tissue to substantial trauma. Often, precise placement of a treatment probe is difficult because of the location of a target tissue in the body or the proximity of the target tissue to easily damaged, critical body organs, nerves, or other components.

Destruction of cellular tissues in situ has been used in the treatment of many diseases and medical conditions alone or as an adjunct to surgical removal procedures. It is often less traumatic than surgical procedures and may be the only alternative where other procedures are unsafe. Ablative treatment devices have the advantage of using a destructive energy which is rapidly dissipated and reduced to a non-destructive level by conduction and convection forces of circulating fluids and other natural body processes.

Microwave, radiofrequency, acoustical (ultrasound), and light energy (laser) devices, and tissue destructive substances have been used to destroy malignant, benign and other types of cells and tissues from a wide variety of anatomic sites and organs. Tissues treated include isolated carcinoma masses and, more specifically, organs such as the prostate, glandular and stromal nodules characteristic of benign prostate hyperplasia. These devices typically include a catheter or cannula which is used to carry a radiofrequency electrode or microwave antenna through a duct to the zone of treatment and apply energy diffusely through the duct wall into the surrounding tissue in all directions.

The copending applications disclose an ablative medical probe generally for penetrating body tissues for medical purposes and a radio frequency medical treatment with optical viewing capabilities.

This RF ablative technology can now be extended to the treatment of uvulas, tonsils, adenoids and sinuses. Many people suffer from inflamed tonsils and adenoids. In addition, many people suffer from sinus problems. In the past, all of these conditions could be treated using surgery. The surgery, however, caused discomfort to the patient and caused bleeding. In addition, surgery required a several day stay at a hospital which is quite expensive.

OBJECTS AND SUMMARY OF THE INVENTION

It is therefore an object of the present invention to provide a method of treating uvula, tonsil, adenoid and sinus tissue which minimizes bleeding and trauma to surrounding tissues.

It is another object of the present invention to provide a device for treating uvula, tonsil, adenoid and sinus tissue which has a disposable electrode.

It is another object of the present invention to provide a method of treating uvula, tonsil, adenoid and sinus tissue in which a medical treatment device is routed through the nasal passages to treat the tissues.

These and other objects of the present invention are provided by a method for medical ablation of tissue to reduce the size and mass of said tissue having the steps of: a) inserting a probe through a body opening and moving the probe into close proximity to the tissue, the probe having an electrode enclosed within an insulating sleeve axially moveable thereon and bendable therewith; b) extending said sleeve and said electrode out of said probe and penetrating said tissue; c) retracting said sleeve from the terminus of the electrode to expose a predetermined electrode area for ablation; and d) applying RF energy to the tissue surrounding the exposed electrode area to effect ablation of said tissue. A device for treating tissue is also disclosed.

DETAILED DESCRIPTION OF THE INVENTION

Figure 1:
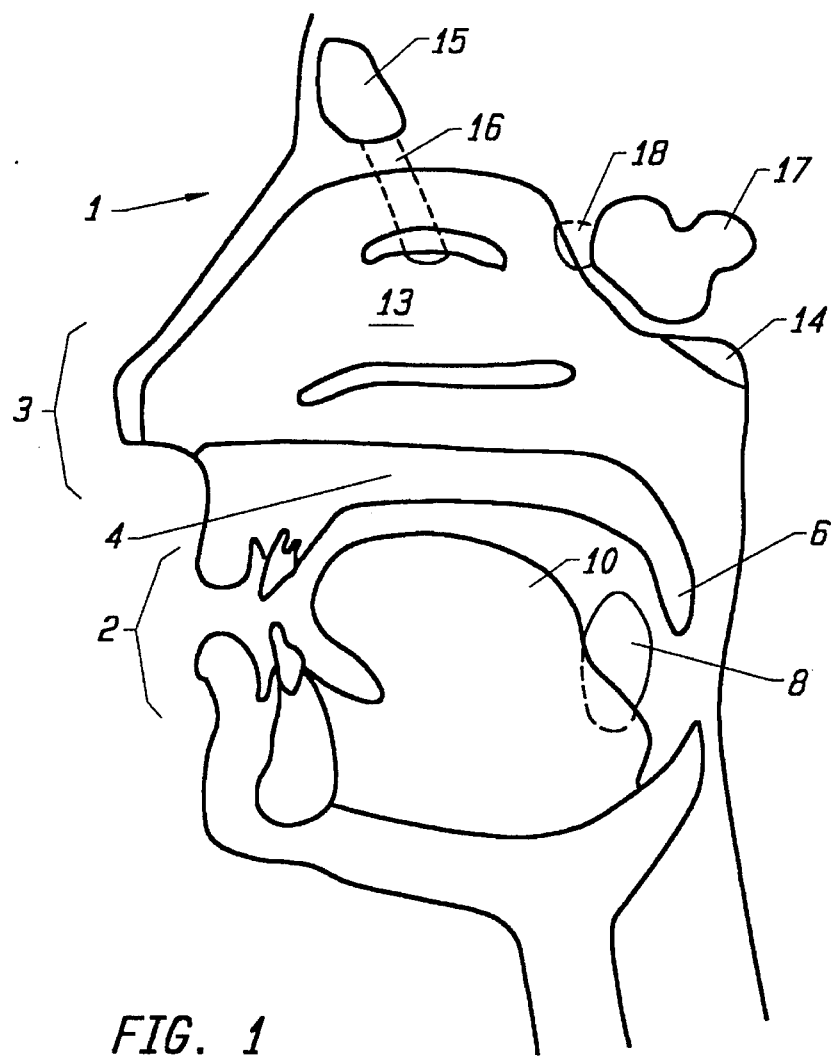
FIG. 1 is a sagittal view of a human head showing the location of the uvula, the tonsils, the adenoids and the sinus tissues.

To understand the device and method of the present invention, a brief look at the anatomy of a human head is needed. FIG. 1 shows a sagittal view of a human head 1. A nose 3 is shown which allows a surgeon access to nasal passages 13. A mouth 2 is also shown. Through the mouth 2, the palate 4 is located. At the end of the palate 4, the uvula 6 is located. The uvula 6 can be accessed either through the mouth 2 or through the nose 3. Located in the mouth 2 behind the tongue 10 is the tonsils 8. Only one tonsil is shown in this figure. The nasal passages 13 have openings 16 and 18 which lead to the frontal sinus 15 and sphenoidal sinus 17, respectively. In addition, adenoid tissue ! can also be accessed through the nasal passages !.

Many problems and diseases can arise within the mouth and nose. For example, a condition known as tonsillitis (i.e., inflamed tonsils) can occur. Also, sinusitis (i.e., inflamed sinus tissues) can also occur. In addition, people develop inflamed adenoids. A person may also have a uvula which is inflamed or needs to be reduced to prevent snoring.

In the past, surgical procedures were available to deal with all of these problems. However, surgery has many risks and causes bleeding. The devices and methods of the present invention can cure the above health problems and reduce recovery time and bleeding.

The first embodiment of the present invention is used for reducing uvular tissue to prevent snoring.

Figure 2:
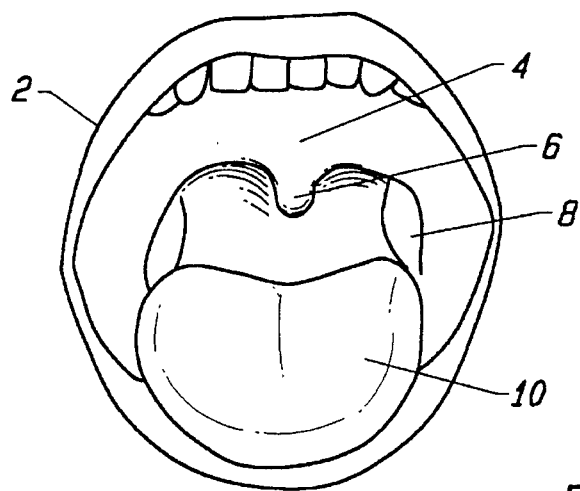
FIG. 2 is a front view of a mouth showing the orientation of the uvula and tonsils.

FIG. 2 shows a front view of a patient's mouth. The cone shaped piece of tissue which hangs down from the palate in the back of the mouth 2 is called the uvula 6. In addition, for reference, a tongue 10 and a pair of tonsils 8 are shown in relation to the uvula 6.

Certain patients lie on their backs when sleeping and at certain times may breathe through their mouth. The movement of the air through the mouth to the lungs may cause the uvula 6 to vibrate and generate a hard, raspy sound that can be very loud at times. This sound is often referred to as a snore. The sleeping patient may not even be aware of snoring until informed by others. In certain other patients, the uvula 6 is large enough to hang down over the throat, effectively blocking the flow of air to the lungs. The patient then gasps for air and possibly wakes up startled and rolls over. Thus, snoring and its problems can be uncomfortable to the patient and certainly disquieting to the patient's bed partner as well.

Apart from the physical, external devices used to wake up the patient, or at least cause the snorer to roll over, there are surgical procedures that can be performed. A uvulectomy or partial uvulectomy can be performed to remove all or part of a patient's uvula. Any surgery, however, has its inherent risks, no matter how fit and healthy the patient may be. Also, the recovery time is extensive due to the bleeding and suturing that must be performed during the surgery. In addition, considerable pain and discomfort is caused to the patient. This conventional uvulectomy can be performed by normal scalpel excising or possibly by use of a strong laser light which is used to destroy part or all of the uvula tissue.

In order to decrease the pain, discomfort and recovery time of the patient, radio frequency (RF) or microwave ablative techniques can be used. In an RF ablative technique, an RF signal from an electrode placed inside the uvula tissue heats the tissue. The cells are heated to a point where the cells burst and die. In fact, the RF ablative technique causes a small lesion within the uvula which is absorbed by the body. Thus, no external bleeding occurs and no suturing is required. Also, the uvula size is decreased.

The medical ablation method utilized in this invention is uniquely superior for localized therapeutic ablation to remove or reduce undesired tissue masses in uvulas in order to reduce snoring.

To fully understand this method of reducing snoring using ablation, a description of an ablation device, as disclosed in the copending applications, follows.

Figure 3:
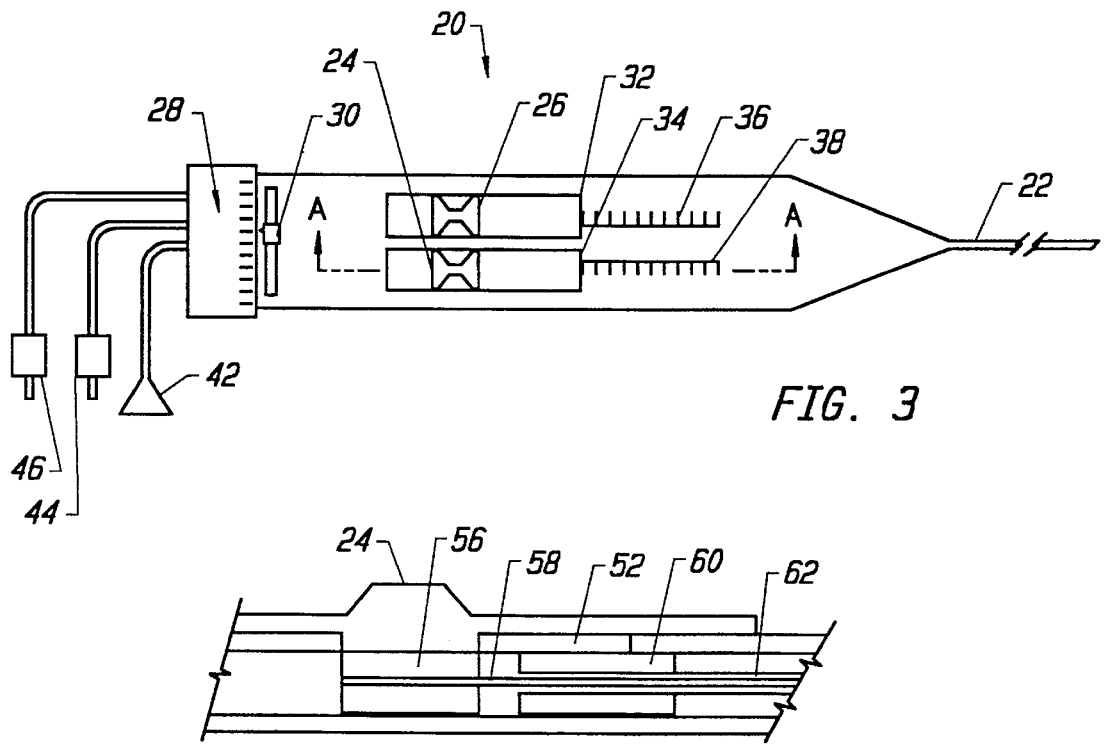
FIG. 3 is a planar view of a stylet ablation device of this invention.
Figure 4:
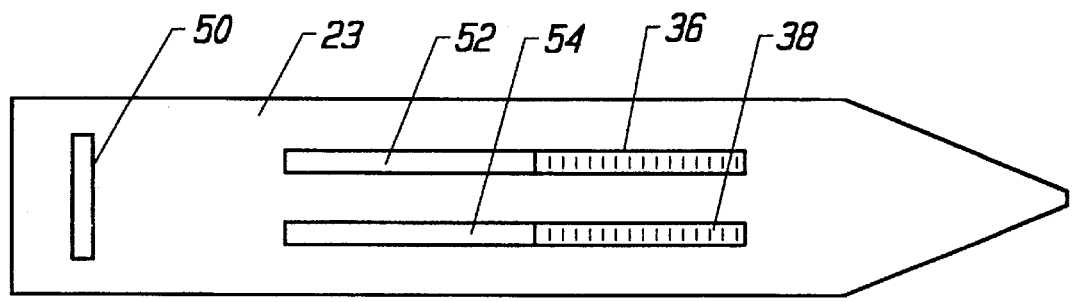
FIG. 4 is a top view of the handle top plate of the stylet ablation device shown in FIG. 3.

Now, the particular structure of the ablation device will be described with reference to FIGS. 3 and 4. FIG. 3 is a planar view of the ablation device. The device generally has a handle portion 20 and a delivery tube portion 22. A stylet sleeve manual control tab 26 and a stylet electrode manual control tab 24 are mounted for sliding engagement in slots 52 and 54 of a handle top plate 23 (FIG. 4). Index markings 28 indicate the relative angle of orientation of the stylet with respect to a stylet angle indicator 30. The angle indicator 30 can be a bubble in a curved transparent tube, a weighted pivot dial indicator or an electronic angle indicator. The position of distal edges 32 and 34 of the tab slides 24 and 26 with their respective gauge reference strips 36 and 38 show the relative positions of a stylet electrode 58 and a sleeve 62 shown in FIGS. 5 and 6. A more detailed description of the operation of the tab slides and reference gauge is below.

Connectors for a fiber optic connector 42, an RF power connector 44, and an ohmic resistance connector 46 extend from the proximal end of the handle portion 20. The connectors connect the ablative device of the present invention to a light source, a power source and a detector, respectively.

FIG. 4 is a top view of the handle top plate 23 of the ablation device shown in FIG. 3. As discussed above, slots 52 and 54 receive the respective tabs 24 and 26 for sliding engagement therein. Slot 50 receives the stylet angle indicator 30. The reference strips 36, 38 are also shown.

Figure 5:
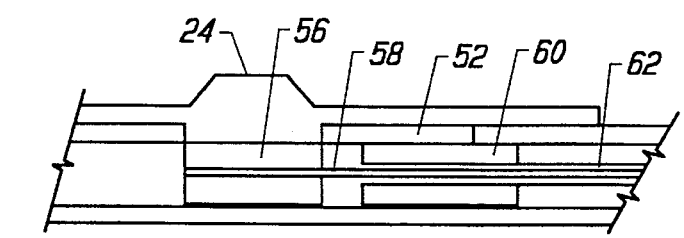
FIG. 5 is a fragmentary cross-sectional view of the manual control portion of the handle of the stylet ablation device shown in FIG. 3 taken along the line A—A in FIG. 3.

Now the structure of the manual tabs 24,26 will be described. FIG. 5 is a fragmentary cross-sectional side view of the manual control portion of the handle of the stylet ablation device shown in FIG. 3, taken along the line A—A.

Since FIG. 5 is a side view, only the electrode manual control tab 24 is shown since the sleeve manual control tab 26 is directly behind the electrode manual control tab 24. The electrode manual control tab 24 is connected to an electrode connector 56. The electrode connector 56 is in turn connected to an electrode 58. Although not shown, the electrode 58 would also be electrically connected to the RF power connector 44 and the ohmic resistance connector 46. The electrode 58 slides inside of a sleeve 62. The sleeve 62 is connected to a sleeve connector 60 which in turn is connected to the sleeve manual control tab 26. Thus, the electrode 58 and the sleeve 62 slide relative to each other.

The electrode 58 is preferably made of a flexible, shape memory metal such as nickel-titanium alloy or tempered steel, but may be of any material which will conduct RF power. The sleeve 62 is preferably made of a highly conformable insulating plastic material such as polyamide. Now, the operation of the tabs 24, 26 will be described.

Simultaneous forward or rearward movement of both manual control tabs 24 and 26 cause the simultaneous advancement and retraction of both the electrode 58 and the sleeve 62. If the electrode manual control tab 24 is moved alone, then the electrode 58 slides within the sleeve 62 and either retracts into or extends out of the sleeve 62. Similarly, if only the sleeve manual control tab 26 is moved, the sleeve slides over the electrode. The reference strips 36 and 38 provide reference points for controlled positioning of the electrode manual control tab 24 and the sleeve manual control tab 26, permitting precise, independent positioning of both the electrode 58 and the sleeve 62 for controlled ablation of the uvula as is explained in greater detail below.

Figure 6:
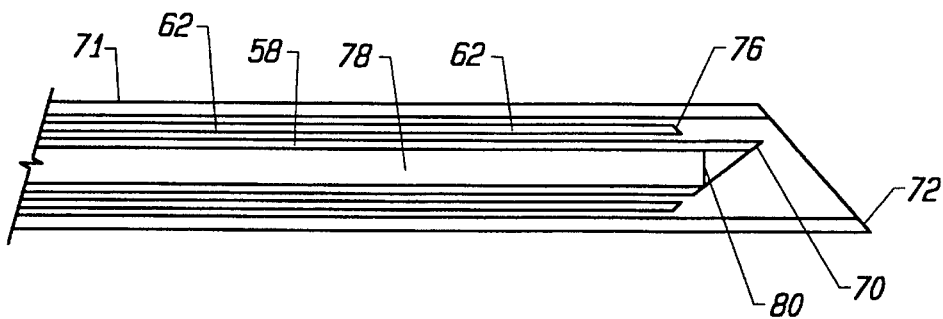
FIG. 6 is a fragmentary cross-sectional view of the tip of the stylet ablation device such as that shown in FIG. 3 with the stylet retracted into the tip.

FIG. 6 is a cross-sectional view of the tip of the ablation device such as that shown in FIG. 3 with the stylet retracted into the tip of a needle 74 for initial insertion to a position accessible with a straight needle. The electrode tip 70 is positioned behind the leading sharpened tip 72 of the needle 74. The insulating sleeve tip 76 is positioned just behind the leading edge of the electrode tip 70.

When the electrode 58 is a hollow tube, it can be a conduit for aspiration during treatment, liquid delivery, or in the embodiment shown, a housing for a fiber optic strand 78. The polished fiber optic tip 80 is positioned behind the electrode tip 70 to facilitate viewing of the tissue surrounding the electrode tip during insertion.

Figure 7:
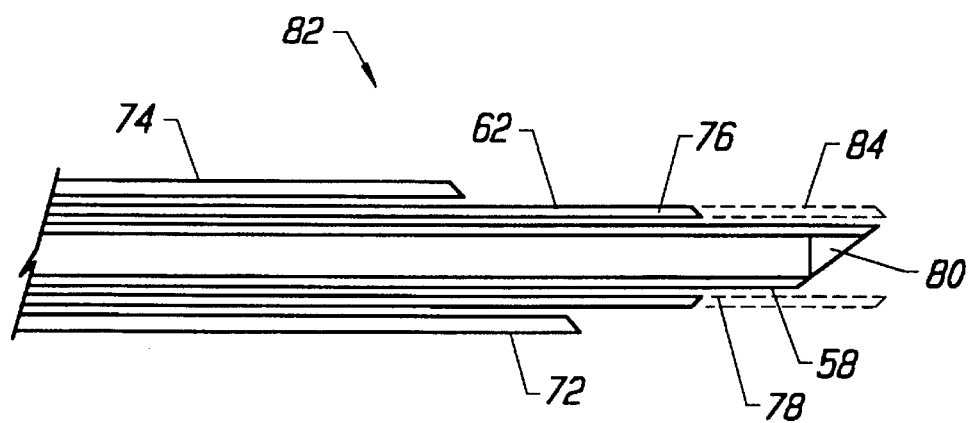
FIG. 7 is a fragmentary cross-sectional view of the tip of the stylet ablation device shown in FIG. 3 with the electrode and sleeve extended from the tip.

FIG. 7 is a cross-sectional view of the tip of the stylet ablation device shown in FIG. 6 with the electrode and sleeve extended out of the needle 74. This embodiment shows a needle 74 having a straight configuration. The needle 74 can also be curved. The sleeve 62 is initially in the dotted line position 84 in which it covers the electrode. Following insertion of the needle 74 into the body to the specific site to be ablated, the sleeve 62 is retracted from a selected portion of the electrode 58 to expose the specific electrode area required to form a lesion of the desired size. The retraction of the sleeve 62 is controlled by the sleeve manual control tab 26 as described above.

Figure 8:
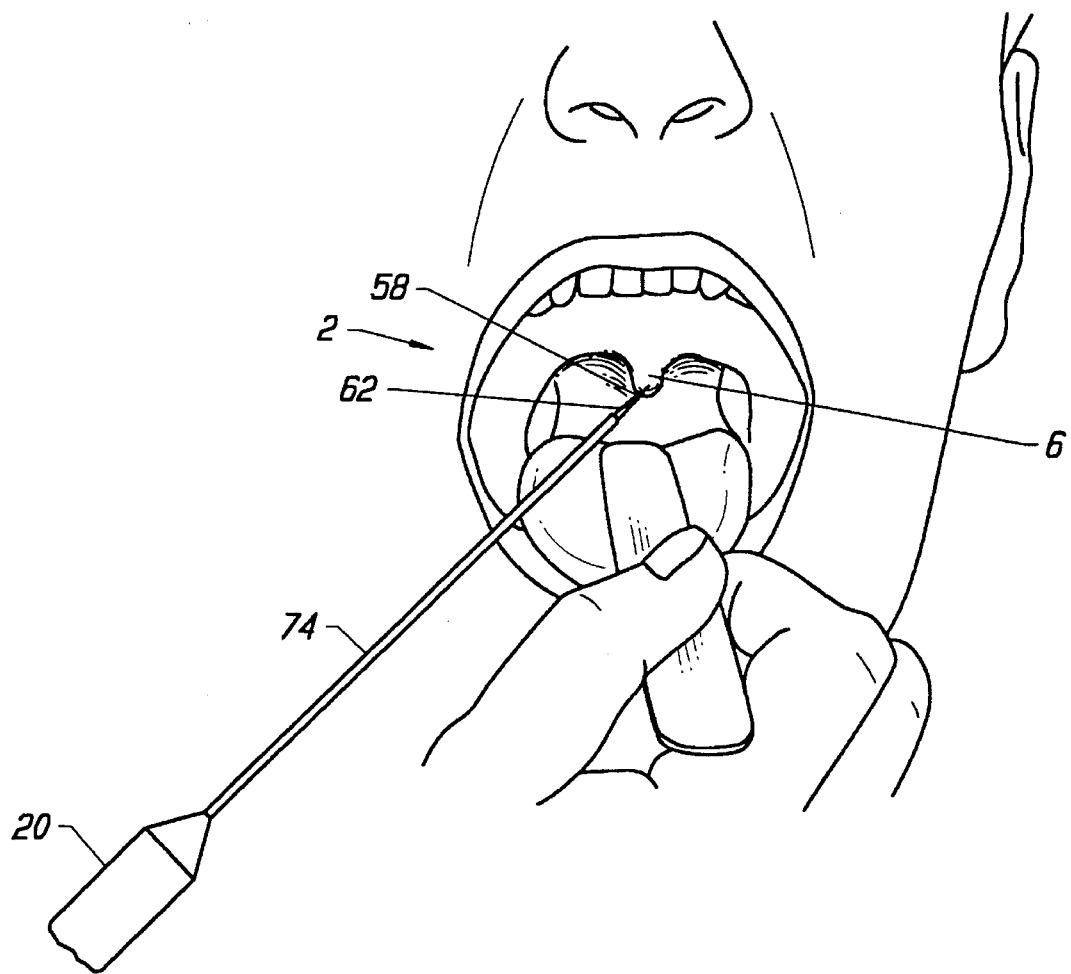
FIG. 8 is a front view of a patient's mouth wherein an uvula is being reduced by the ablative method of the present invention.

FIG. 8 shows a front view of a patient's mouth with the RF ablation device being used to treat an uvula 6 according to the present method. The patient opens his/her mouth 2 and the tongue is held down. The RF ablative device with the handle portion 20 is positioned so that the needle 74 is near the uvula 6. The sleeve 62 and electrode 58 are then extended out of the needle 74 and into the uvula 6. Then, the electrode 58 is exposed by a desired distance, depending on the amount of the uvula to be ablated. Then, RF or microwave energy is sent through the electrode 58 and causes an internal lesion within the uvula 6. Once this internal lesion is absorbed by the body, the size of uvula 6 decreases and further snoring problems are eliminated.

Now, another embodiment of the present invention will be described which can be used to treat tonsil tissue, adenoid tissue, sinus tissue and even uvula tissue. Both a device for treating the tissues and a method of treating the tissues will be described.

Figure 9:
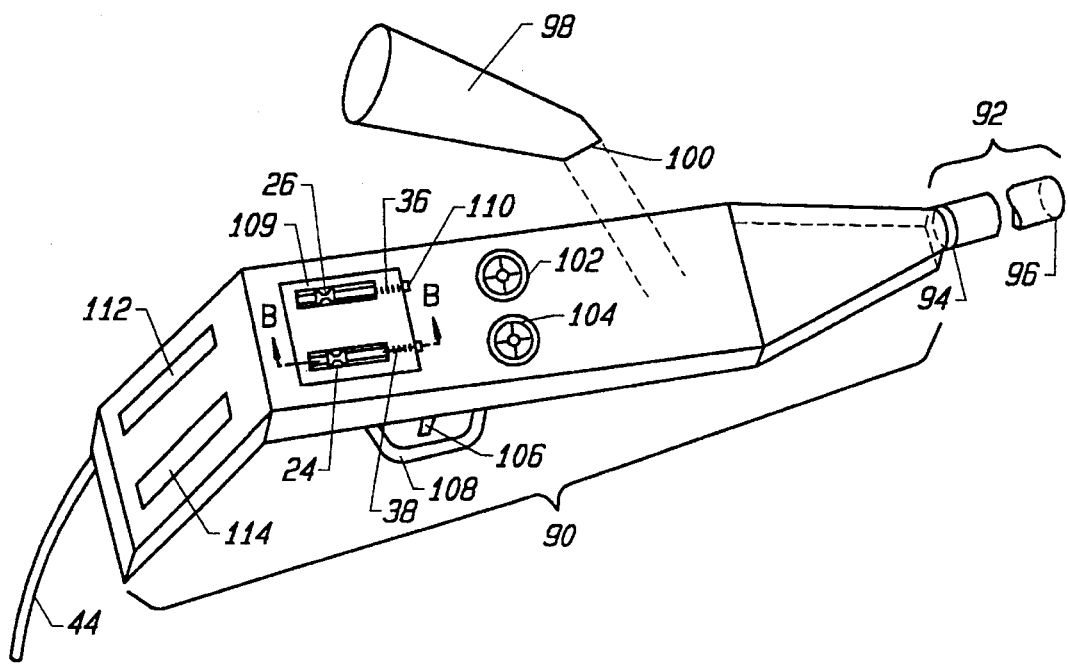
FIG. 9 is an isometric view of the device of the present invention for treating uvulas, tonsils, adenoids and sinus tissues.

FIG. 9 shows a planar view of another embodiment of a device for treating uvula, tonsil, adenoid and sinus tissue. This embodiment has many similar parts to the first embodiment and like parts will be designated by like numerals. The handle portion 90 is connected to a probe 92, which has a handle end 94 and a probe end 96. This device has the same tabs 24, 26 which control an electrode 122 and a sleeve 124. Thus, the operation of the tabs 24, 26 will not be described here. One difference in this embodiment is that the electrode 122 is disposable so that the tabs 24, 26 and the other controller structure are mounted on a surface 109 which opens up on hinges 110. The controller will be described below with reference to FIG. 17.

The device of this embodiment also has an impedance meter 112 and a temperature meter 114 which are incorporated into the handle 90. Both meters 112 and 114 are electrically connected to the RF power supply lead 44 to supply feedback data. These meters allow the surgeon to accurately control the treatment.

The handle 90 also has a trigger 106 and trigger guard 108 which control the energization of the RF power source. The handle 90 also has a viewing scope 98 which is connected by a hinge 100 to the handle 90 so that the viewing scope 98 is adjustable. The viewing scope 98 is connected to the fiber optic 78 which allows the surgeon to view the treatment at all times. The handle 90 also has a horizontal steering control wheel 102 and a vertical steering control wheel 104. The operation of the wheels will be described below with reference to FIG. 10.

Figure 10:
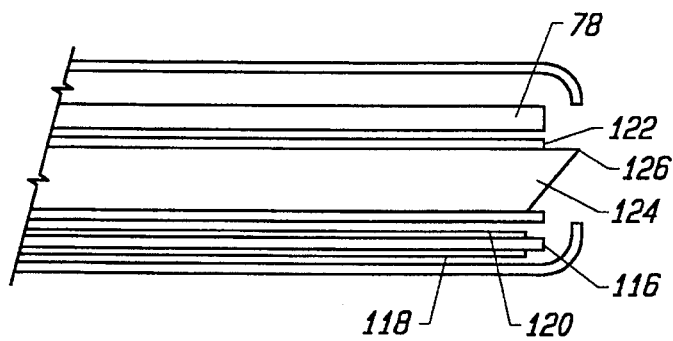
FIG. 10 is an expanded fragmentary cut-away side view of the probe end of the device shown in FIG. 9 having a retracted fiber optic, a retracted electrode, and a steering mechanism.

FIG. 10 is an expanded cut-away side view of the probe end 96 of the device shown in FIG. 9. The probe end 96 is not sharpened in this embodiment so that it can follow a route through the sinus passages without puncturing any tissue. In this embodiment, any tissue puncturing which is required is done by a sharpened tip 126 of the electrode 124. Inside of the probe end 96, there is the electrode 124 with a sharpened tip 126, a sleeve 122 around the electrode, and a fiber optic 78. The sleeve 122 is thin compared to the electrode and located behind the sharpened tip 126 of the electrode. Thus, both the electrode 124 and sleeve 122 together can puncture tissue. Then the sleeve 122 can be retracted to expose the electrode 124. Also, the sleeve 122 can be retracted prior to tissue penetration. In addition, the sleeve 122 may be rigidly fixed to the electrode 124 so that a predetermined amount of the electrode 124 is always exposed. The sleeve 122 protects healthy tissue from damage during the treatment. For example, the sleeve 122 will protect the nasal passages during treatment of the adenoid tissue. There are also steering members which are connected to both of the steering wheels 102 and 104 by steering wires. Only the vertical control wires 118 and 120 and the vertical steering member 116 are shown. It should be understood that the horizontal steering member and steering wires work in the same way. The vertical steering member 116 is attached near the handle end 94. To steer the probe end 96 upwards, the vertical steering wheel 102 is turned and the upper steering wire 120 is pulled back which causes the flexible steering member 116 to bend upwards which causes the probe end 96 to bend also. Similarly, the probe end 96 can be adjusted downwards. It should be noted that the probe end 96, the electrode 124, the sleeve 122, and the fiber optic 78 are all somewhat flexible so they can bend. A more detailed description of the steering mechanism can be found in U.S. Pat. Nos. 5,195,968 and 5,254,088 which are incorporated herein by reference.

Figure 11:
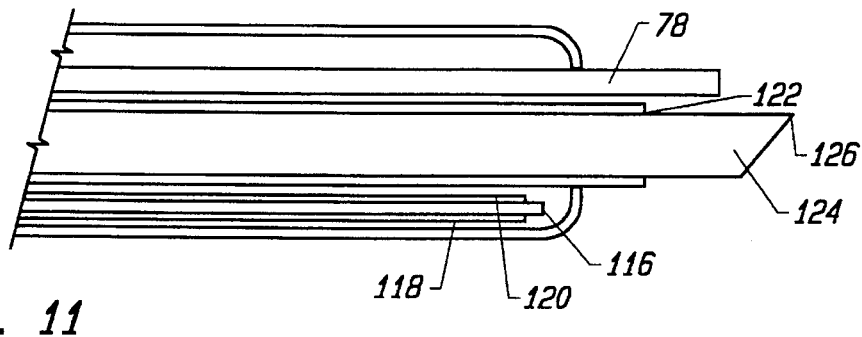
FIG. 11 is an expanded fragmentary cut-away side view of the probe end of the device shown in FIG. 9 having an extended fiber optic, an extended electrode and a steering mechanism.
Figure 12:
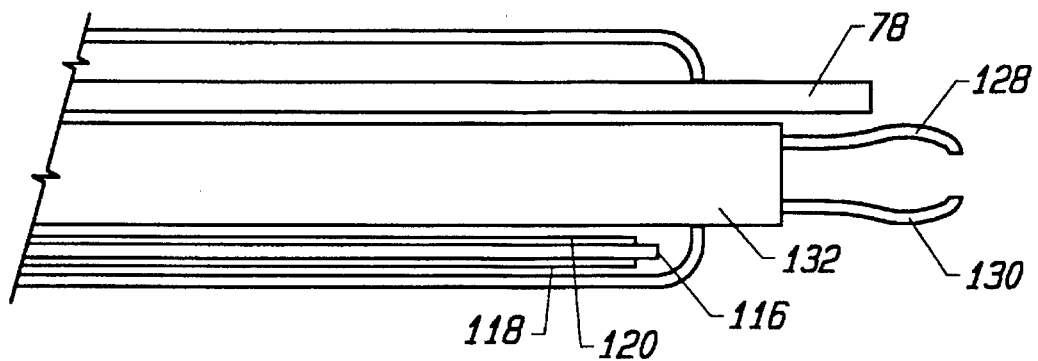
FIG. 12 is an expanded fragmentary cut-away side view of the probe end of the device shown in FIG. 9 having a bipolar electrode and a fiber optic.

FIG. 11 shows the probe end 96 of FIG. 10 with the fiber optic 78, sleeve 122 and electrode 124 extended out of the probe end. FIG. 12 shows another embodiment of the device which has bipolar electrodes 128 and 130 in a single sleeve 132, a fiber optic 78 and steering mechanisms. Unlike monopolar electrodes 124 which requires an external grounding plate, the bipolar electrodes are a first electrode 128 and a second electrode 130. The RF current goes from the first electrode 128 at a voltage $V_1$, through the tissue to be treated and returns through the second electrode 130 at a voltage $V_2$ which is lower than $V_1$. The bipolar electrode can be used with the present invention equally as well as a monopolar electrode.

Figure 13:
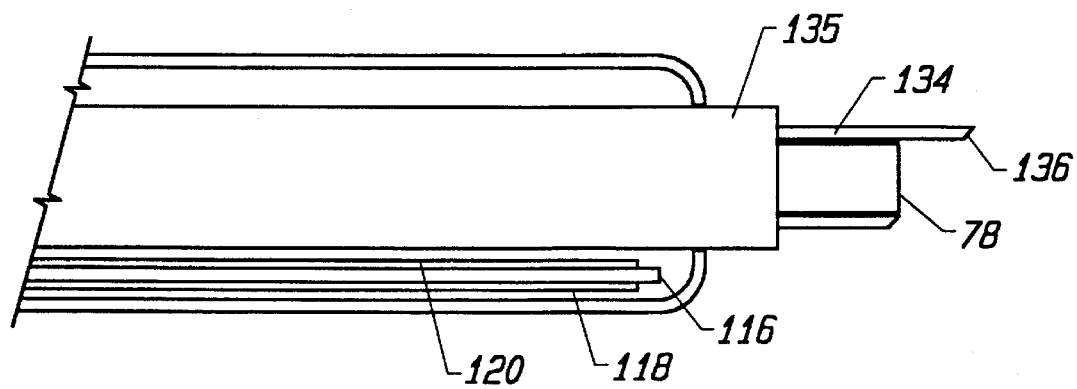
FIG. 13 is an expanded fragmentary cut-away side view of the probe end of the device shown in FIG. 9 having a hollow electrode and a fiber optic housed within the electrode.

FIG. 13 shows another embodiment of the present invention which has a hollow monopolar electrode 134. The hollow monopolar electrode 134 is housed within a sleeve 135 as before. However, inside of the hollow monopolar electrode, a fiber optic 78 is located. As before, a steering mechanism is located within the probe end 96.

Figure 14:
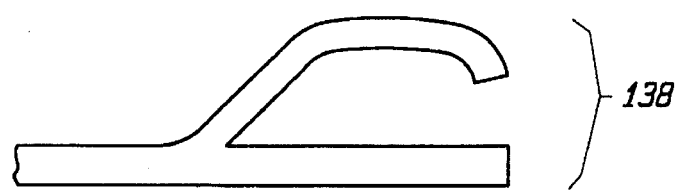
FIG. 14 is an expanded fragmentary side view of one embodiment of a monopolar electrode which is used in the present invention.
Figure 15:
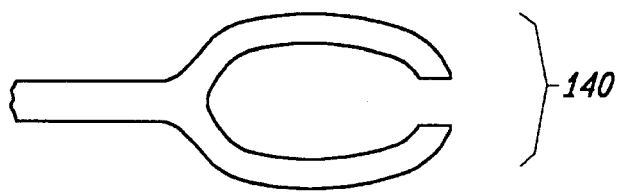
FIG. 15 is an expanded fragmentary side view of another embodiment of a monopolar electrode.
Figure 16:
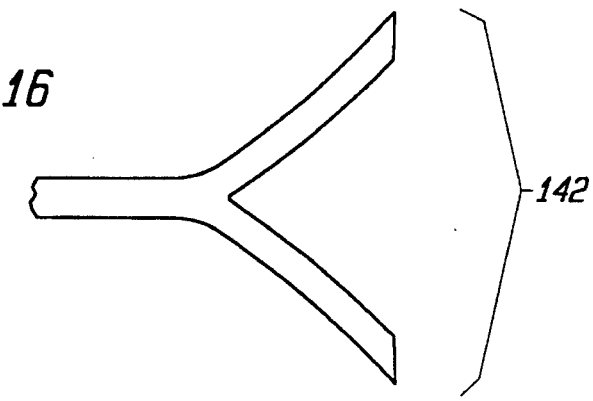
FIG. 16 is an expanded fragmentary side view of another embodiment of a monopolar electrode.

FIGS. 14, 15, and 16 show three different embodiments of a monopolar electrode. FIG. 14 is a pincher electrode 138 which is used to treat uvula or tonsil tissue. When the pincher electrode 138 is within the sleeve, it collapses. Then, when the sleeve is retracted, the pincher electrode 138 takes the shape shown. Similarly, FIG. 15 shows another embodiment of a pincher electrode 140. FIG. 16 shows an electrode 142 having two branches which is used to treat both tonsils in a single treatment.

Figure 17:
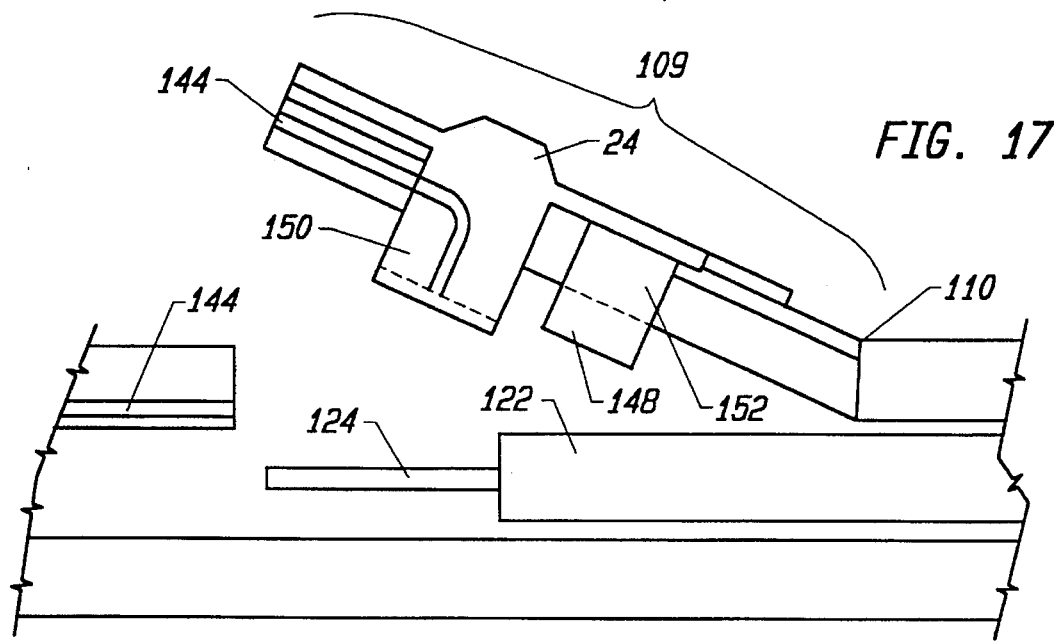
FIG. 17 is a fragmentary expanded cross sectional view of the device shown in FIG. 9 taken along line A—A.

FIG. 17 is an expanded cross-sectional view of the device of FIG. 9 taken along line B—B and shows the hinged surface 109 of the handle which has the tabs 24, 26. As before, only the electrode tab 24 is shown since the sleeve tab 26 is directly behind the other tab. The electrode tab 24 is connected to an electrode connector 150. The electrode connector 150 has an electrical contact 146 which electrically connects the disposable electrode 124 to the connector 150. The connector 150 has an electrical trace 144 which electrically connects the disposable electrode 124 to the RF connector 44 (not shown). The connector 150 also mechanically connects the disposable electrode 124 to the electrode tab 24. Similarly, the sleeve tab is connected to a sleeve connector 152 by a sleeve contact 148 which connects to the sleeve 122.

In operation, after the surgeon has guided the probe end 96 to near the target tissue, a disposable electrode 124 and sleeve 122 are placed within the device through the hinged surface 109. Once the electrode and sleeve are in place, the hinged surface 109 is closed and latched. When the hinged surface 109 is closed and latched, the disposable electrode 124 and sleeve 122 are mechanically and electrically connected to the device. Once the treatment with the particular electrode is complete, the hinged surface 109 is opened and the disposable electrode 124 and sleeve 122 are removed. Then another electrode can be inserted, or the device may be removed.

Figure 18:
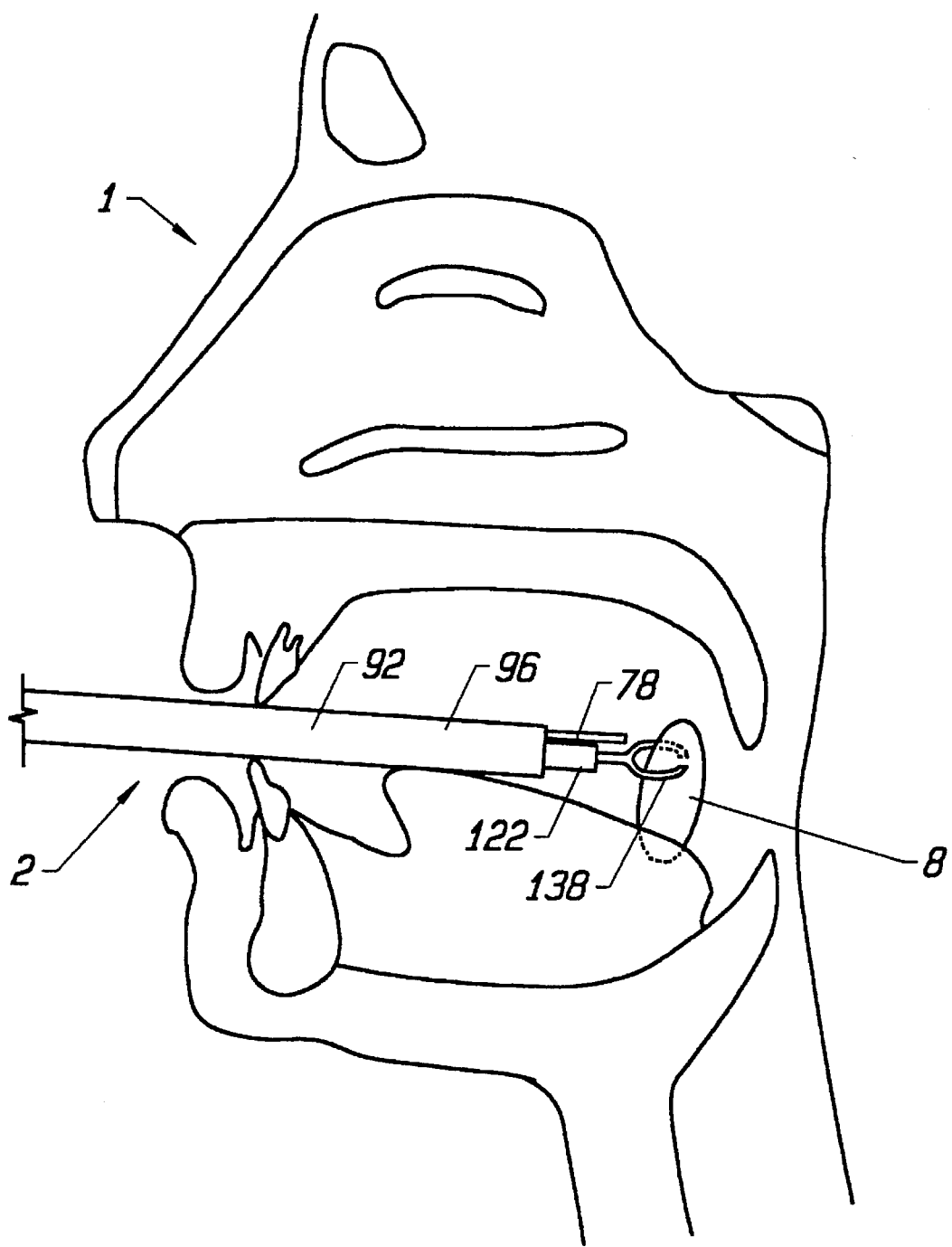
FIG. 18 is a sagittal view of a human head showing the device of the present invention having a monopolar pincher electrode being used to treat a tonsil.

The methods of treating tonsil tissue, adenoid tissue, sphenoidal sinus tissues, frontal sinus tissue and uvula tissue will now be described with reference to FIGS. 18–23. FIG. 18 is a sagittal view of a head showing the probe 92 inserted through the mouth 2 to treat a tonsil 8. The probe end 96 is positioned by the surgeon near the tonsil 8 and the fiber optic 78, electrode 124 and sleeve 122 are extended out of the probe end 96. Then, the pincher electrode 138 is extended out of the sleeve 122 and surrounds the tonsil 8. Then, RF current flows through the electrode 124 and causes an internal lesion within the tonsil 8. If enough power is supplied to the tonsil 8, all of the tonsil tissue can be eliminated. In both cases, the temperature of the tissue must be raised to above 47° C. for a sufficient time to cause death of the tissue cells. No significant bleeding occurs and the tonsil 8 has been treated.

Figure 19:
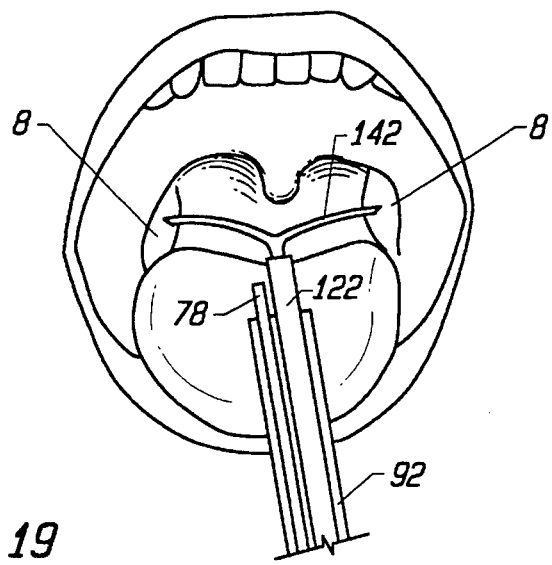
FIG. 19 is a front view of a mouth showing the device of the present invention being used to treat a pair of tonsils with one monopolar electrode.

Similarly, in FIG. 19, the probe is inserted through the mouth 2 and the branched electrode 142 is used to treat both tonsils simultaneously. The branched electrode 142 has sharpened tips so that the electrodes can penetrate the tonsils and generate an RF current within the tonsil. Once again, the RF current creates a lesion within the tonsils.

Figure 20:
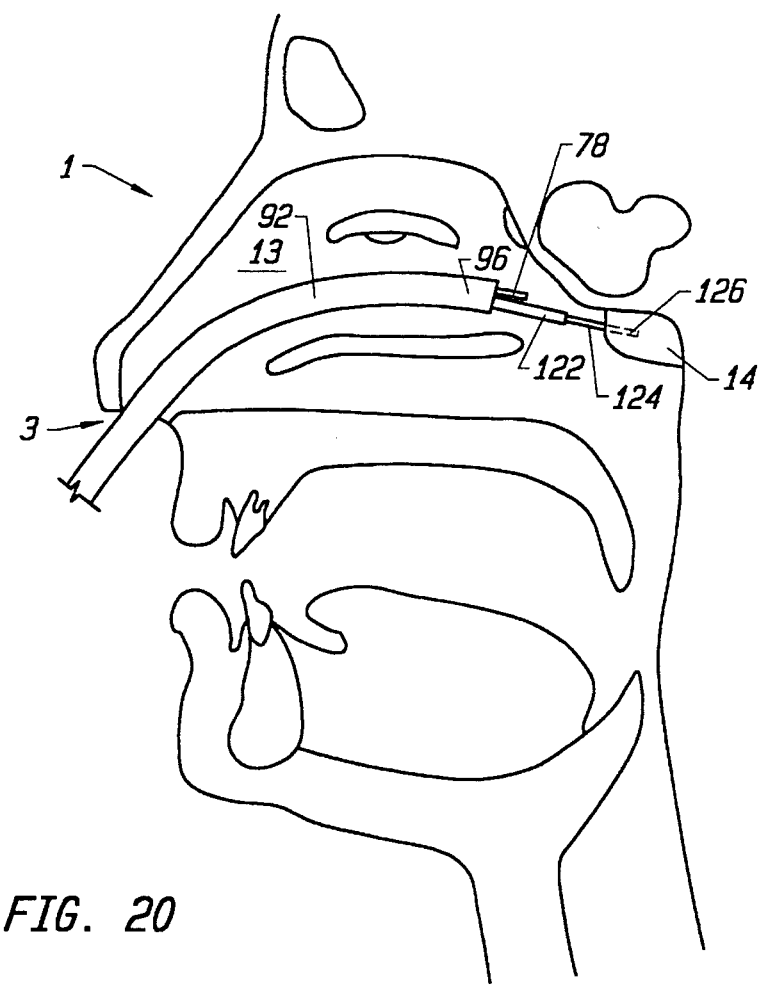
FIG. 20 is a sagittal view of the head of a person showing the device of the present invention being used to treat an enlarged adenoid.

FIG. 20 shows the probe inserted through the nose 3 and the nasal passages 13 to treat adenoids 14. For this treatment, the fiber optic 78 is used to help the surgeon guide the probe end 96 to a location near the adenoid 14 using the steering wheels, if necessary. Once near the adenoid 14, the surgeon extends the fiber optic 78 and sleeve 122 out towards the adenoid 14. Then, the electrode 124 is extended out of the sleeve 122 until the sharpened tip 126 of the electrode penetrates the adenoid 14 to a desired depth. Then, the RF current is supplied to the tissue by the electrode and a lesion is formed within the adenoid. Once the body reabsorbs the lesion, the adenoid 14 shrinks or is eliminated.

Figure 21:
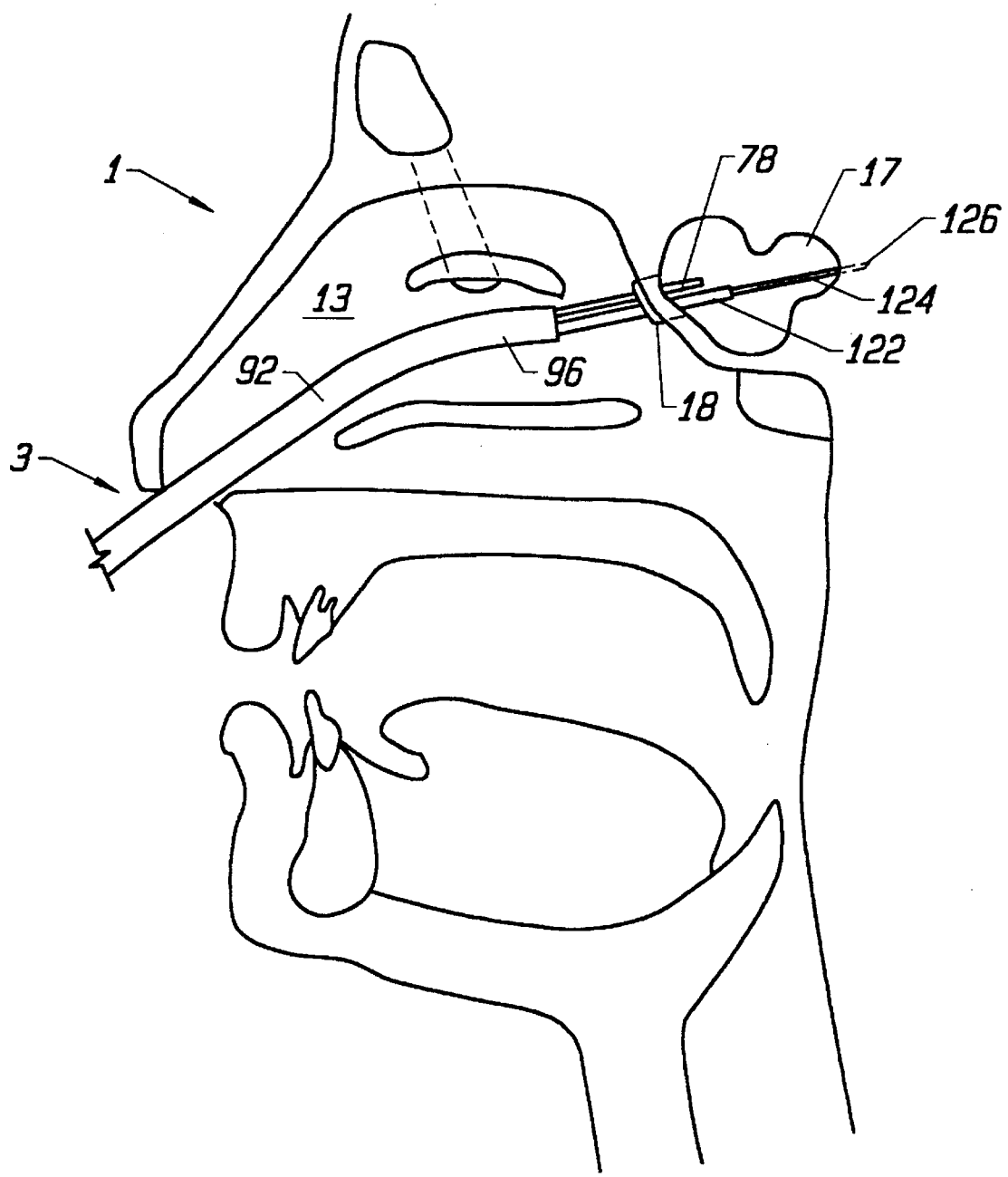
FIG. 21 is a sagittal view of a head of a person showing the device of the present invention being used to treat rear sinus tissue.
Figure 22:
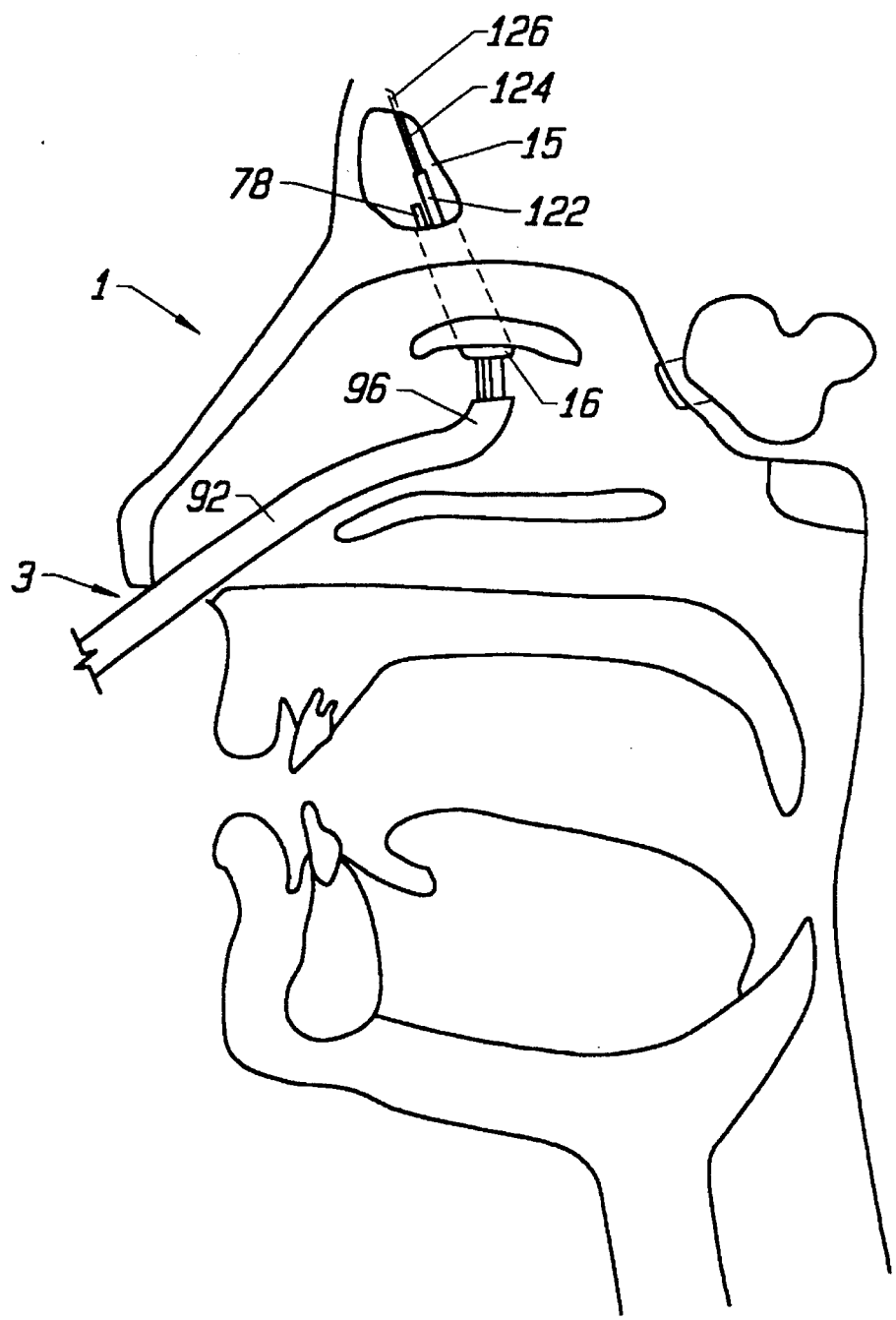
FIG. 22 is a sagittal view of a head of a person showing the device of the present invention being used to treat frontal sinus tissue.

FIG. 21 shows the probe inserted through the nose ! and nasal passages 13 to treat the sphenoidal sinus tissue 17. As before, the surgeon uses the steering wheels 102 and 104 to adjust the direction of the probe end 96 and guide the probe end near the opening 18 of the sphenoidal sinus 17. Then, the fiber optic 78 and sleeve 122 with electrode are extended through the opening 18 into the sphenoidal sinus. Then, the sharpened tip 126 of the electrode 124 is extended into the sinus tissue and the treatment is completed. Similarly, FIG. 22 shows the device inserted through the nose 3 and nasal passages 13 to treat the frontal sinus 15. Once again, the probe end 96 is adjusted using the steering wheels 102 and 104 so that it is correctly positioned near the opening 16 of the frontal sinus 15. As before, the fiber optic 78 and sleeve 122 are extended through the opening 16 and the sharpened tips 126 of the electrode 124 is extended into the tissue and RF power is supplied to treat the tissue.

Figure 23:
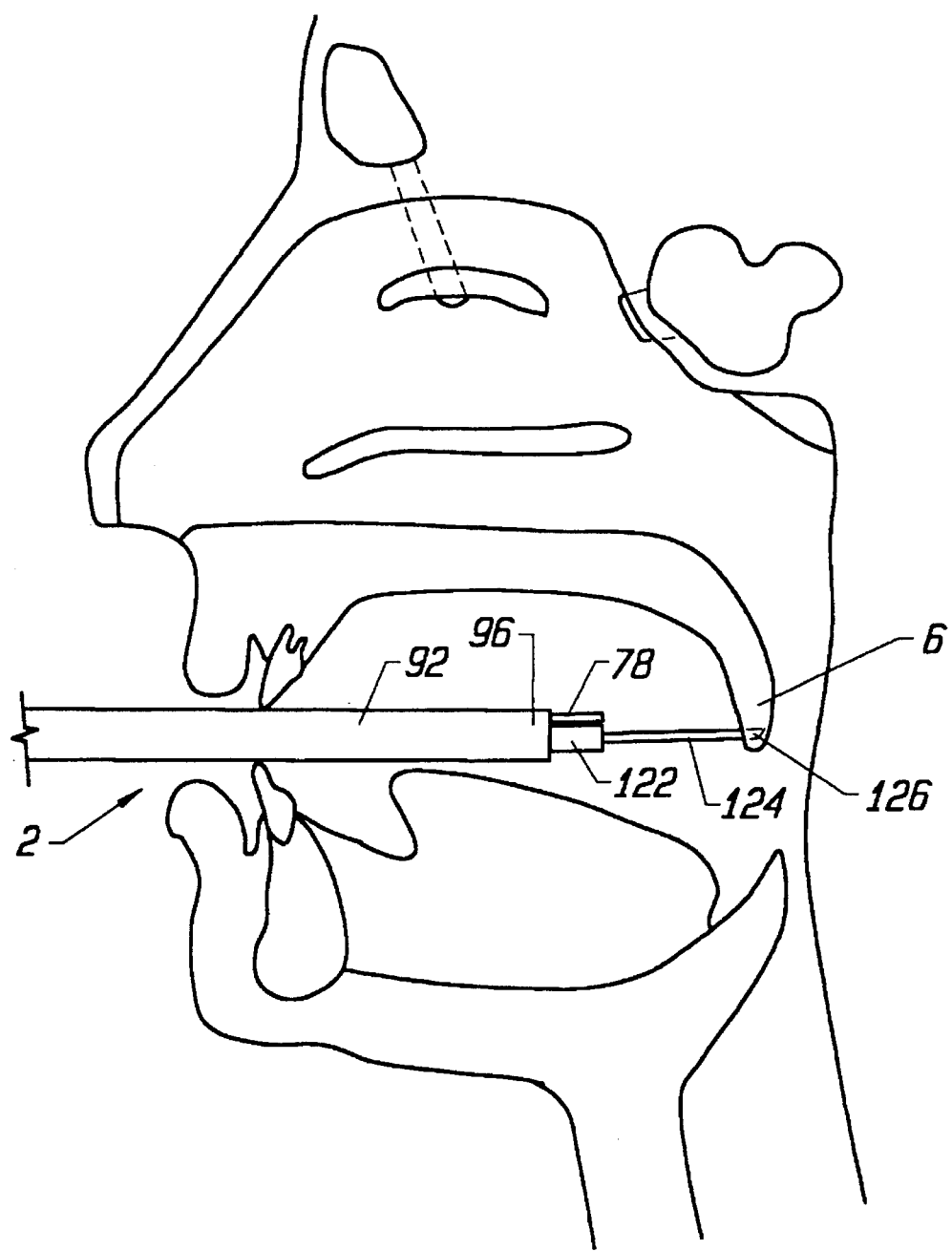
FIG. 23 is a sagittal view of the head of a person showing the device of the present invention being used to treat the uvula.

FIG. 23 shows the probe inserted through the mouth 2 to treat the uvula 6. The probe end 96 is positioned near the uvula 6 and the fiber optic 78 and sleeve 122 are extended out. Then, the electrode 124 is extended out of the sleeve and the sharpened tip 126 of the electrode penetrates the uvula and treatment is carried out.

While the invention has been described with reference to specific preferred embodiments, it will be understood by those skilled in the art that various changes may be made and equivalents may be substituted for elements thereof without departing from the true spirit and scope of the invention. In addition, many modifications may be made without departing from the essential teachings of the invention.

The invention claimed is:

1. A method of ablating a portion of a uvula, comprising:

providing an RF ablation apparatus including a handle, an RF ablation electrode with a distal end sharpened sufficiently to pierce the uvula, an advancement and retraction device coupled to the ablation electrode and an RF energy source coupled to the ablation needle;

introducing at least a portion of the RF ablation apparatus including the ablation electrode distal end into a mouth cavity;

positioning the RF ablation apparatus distal end adjacent to the uvula;

advancing the RF ablation apparatus distal end to pierce the uvula and extend a desired distance within the uvula;

applying RF ablation energy to the ablation electrode;

forming an ablation lesion within the uvula; and retracting the RF ablation electrode distal end from the uvula.

2. The method of claim 1, wherein the distal end of the RF ablation electrode is sufficiently sharpened to pierce the uvula while it is unsupported to remain in a stationary position.

3. The method of claim 1, wherein the RF ablation electrode is a needle electrode.

4. The method of claim 1, wherein the RF ablation apparatus operates in a bipolar mode.

5. The method of claim 1, wherein the RF ablation apparatus includes a second RF ablation electrode.

6. The method of claim 1, wherein the RF ablation apparatus operates in a monopolar mode.

7. The method of claim 1, wherein the RF ablation apparatus includes a ground pad electrode coupled to the RF energy source.

8. The method of claim 1, wherein the distal end of the RF ablation electrode is introduced and advanced in and out of the uvula during two or more successive ablations.

9. A method of ablating a portion of a uvula, comprising:

providing an RF ablation apparatus including a handle, a stylet coupled to the handle and including a sharpened distal end, an RF ablation electrode with a distal end slideably positioned in an interior lumen of the stylet, an advancement and retraction device coupled to one of the ablation electrode or the stylet, and an RF energy source coupled to the ablation needle;

introducing at least a portion of the RF ablation apparatus including the stylet distal end into a mouth cavity;

positioning the stylet distal end adjacent to the uvula;

advancing the stylet and RF ablation apparatus distal ends into the uvula and extending the RF ablation apparatus distal end a desired distance within the uvula;

applying RF ablation energy to the ablation electrode;

forming an ablation lesion within the uvula; and retracting the stylet and RF ablation electrode distal ends from the uvula.

10. The method of claim 9, wherein the distal end of the stylet is sufficiently sharpened to pierce the uvula while it is unsupported to remain in a stationary position.

11. The method of claim 9, wherein the RF ablation electrode is a needle electrode.

12. The method of claim 9, wherein the RF ablation apparatus operates in a bipolar mode.

13. The method of claim 9, wherein the RF ablation apparatus includes a second RF ablation electrode.

14. The method of claim 9, wherein the RF ablation apparatus operates in a monopolar mode.

15. The method of claim 9, wherein the RF ablation apparatus includes a ground pad electrode coupled to the RF energy source.

16. The method of claim 9, wherein the distal end of the RF ablation electrode is introduced and advanced in and out of the uvula during two or more successive ablations.

* * * * *

UNITED STATES PATENT AND TRADEMARK OFFICE
CERTIFICATE OF CORRECTION

PATENT NO. : 5,514,131

DATED : May 7, 1996

INVENTOR(S) :
Stuart D. Edwards, David L. Douglass

It is certified that error appears in the above-indentified patent and that said Letters Patent is hereby corrected as shown below:

Abstract, first sentence: change "accessible thorough" to –accessible through—

Col 3, line 49, change "adenoid tissue !" to –adenoid tissue 14—

Col 3, line 50, change "passages !" to –passages 13—

Col 5, line 41, change "needle 74" to –needle 71—

Col 5, line 44, change "needle 74" to –needle 71—

Col 6, line 22, change "electrode 122 and a sleeve 124" to –electrode 124 and a sleeve 122—

Col 6, line 25, change "122" to –124—

Col 6, line 54, change "thin" to –then—

Col 8, line 38, change "nose !" to –nose 3—

Col 8, line 49, change "corrected" to --correctly—

Signed and Sealed this

Thirtieth Day of September, 1997

Attest:

BRUCE LEHMAN

Attesting Officer

Commissioner of Patents and Trademarks